United States Patent
Sanchez et al.

(10) Patent No.: US 9,603,742 B2
(45) Date of Patent: Mar. 28, 2017

(54) REMOTE MAGNETIC DRIVEN FLOW SYSTEM

(71) Applicant: Novartis AG, Basel (CH)

(72) Inventors: Robert Sanchez, Oceanside, CA (US); Casey Lind, Orange, CA (US)

(73) Assignee: Novartis AG, Basel (CH)

( * ) Notice: Subject to any disclaimer, the term of this patent is extended or adjusted under 35 U.S.C. 154(b) by 260 days.

(21) Appl. No.: 14/208,237

(22) Filed: Mar. 13, 2014

(65) Prior Publication Data

US 2015/0257931 A1 Sep. 17, 2015

(51) Int. Cl.
 *A61F 9/00* (2006.01)
 *A61F 9/007* (2006.01)
 *A61B 5/03* (2006.01)

(52) U.S. Cl.
 CPC .......... *A61F 9/00781* (2013.01); *A61B 5/036* (2013.01); *A61B 2560/0257* (2013.01)

(58) Field of Classification Search
 CPC .. A61M 27/00; A61M 27/006; A61F 9/00781
 See application file for complete search history.

(56) References Cited

U.S. PATENT DOCUMENTS

| | | |
|---|---|---|
| 4,089,329 A | 5/1978 | Couvillon et al. |
| 4,206,762 A | 6/1980 | Cosman |
| 4,457,757 A | 7/1984 | Molteno |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters et al. |
| 5,005,577 A | 4/1991 | Frenkel |
| 5,083,742 A | 1/1992 | Wylie et al. |
| 5,098,409 A | 3/1992 | Stock |

(Continued)

FOREIGN PATENT DOCUMENTS

| | | |
|---|---|---|
| DE | 4438201 A1 | 5/1996 |
| WO | 9303665 A1 | 2/1993 |

(Continued)

OTHER PUBLICATIONS

Bae et al. In vitro experiment of the pressure regulating valve for a glaucoma implant; J. Micromech. Microeng. 13 (2003) 613-619.*

(Continued)

*Primary Examiner* — Tatyana Zalukaeva
*Assistant Examiner* — Benjamin Klein
(74) *Attorney, Agent, or Firm* — Kenneth D. Bassinger

(57) ABSTRACT

A system for implantation in an eye of a patient includes a flow device sized for implantation into the eye of the patient. The flow device includes a fluid flow passageway and a flow system. The flow system may include a regulator having a magnetic element, and may be displaceable in the fluid flow passageway to affect flow through the fluid flow passageway. The system may also include a control device physically separate from the flow device and configured to be disposed outside the eye, the control device comprising an actuator magnetic field generator configured to act on the magnetic element to adjust the regulator in the flow system to selectively adjust flow through the flow device in response to changes in intraocular pressure.

20 Claims, 4 Drawing Sheets

(56) References Cited

U.S. PATENT DOCUMENTS

| | | | |
|---|---|---|---|
| 5,178,604 A | 1/1993 | Baerveldt et al. |
| 5,179,953 A | 1/1993 | Kursar |
| 5,397,300 A | 3/1995 | Baerveldt et al. |
| 5,466,233 A | 11/1995 | Weiner |
| 5,476,445 A | 12/1995 | Baerveldt et al. |
| 5,558,629 A | 9/1996 | Baerveldt et al. |
| 5,573,646 A | 11/1996 | Saito |
| 5,626,558 A | 5/1997 | Suson |
| 5,681,275 A | 10/1997 | Ahmed |
| 5,707,643 A | 1/1998 | Ogura |
| 5,910,110 A | 6/1999 | Bastable |
| 6,007,511 A | 12/1999 | Prywes |
| 6,048,328 A | 4/2000 | Haller |
| 6,251,090 B1 | 6/2001 | Avery |
| 6,261,256 B1 | 7/2001 | Ahmed |
| 6,447,449 B1 | 9/2002 | Fleischman |
| 6,468,283 B1 | 10/2002 | Richter |
| 6,579,235 B1 | 6/2003 | Abita |
| 6,589,198 B1 | 7/2003 | Soltanpour |
| 6,682,500 B2 | 1/2004 | Soltanpour |
| 6,712,764 B2 | 3/2004 | Jeffries |
| 6,719,750 B2 | 4/2004 | Varner et al. |
| 6,749,568 B2 | 6/2004 | Fleischman |
| 6,939,299 B1 | 9/2005 | Petersen |
| 6,976,982 B2 | 12/2005 | Santini et al. |
| 7,137,952 B2 | 11/2006 | Leonardi |
| 7,169,106 B2 | 1/2007 | Fleischman |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,612,328 B2 | 11/2009 | Kaiser |
| 7,756,559 B2 | 7/2010 | Abreu |
| 7,824,699 B2 | 11/2010 | Ralph et al. |
| 8,182,435 B2 | 5/2012 | Dacquay et al. |
| 8,257,295 B2 | 9/2012 | Rickard et al. |
| 8,419,673 B2 | 4/2013 | Rickard |
| 9,283,115 B2* | 3/2016 | Lind ............... A61F 9/00781 |
| 2001/0000527 A1 | 4/2001 | Yaron |
| 2002/0013545 A1* | 1/2002 | Soltanpour ......... A61F 9/00781 |
| | | | 604/9 |
| 2002/0019607 A1 | 2/2002 | Bui |
| 2002/0049374 A1 | 4/2002 | Abreu |
| 2002/0087111 A1 | 7/2002 | Ethier |
| 2002/0099359 A1 | 7/2002 | Santini et al. |
| 2002/0139947 A1 | 10/2002 | Wang |
| 2002/0143284 A1 | 10/2002 | Tu et al. |
| 2002/0193674 A1 | 12/2002 | Fleischman |
| 2003/0014036 A1 | 1/2003 | Varner et al. |
| 2003/0078487 A1 | 4/2003 | Jeffries |
| 2003/0225318 A1 | 12/2003 | Montegrande |
| 2004/0013702 A1 | 1/2004 | Glover |
| 2004/0059248 A1 | 3/2004 | Messner |
| 2004/0073137 A1 | 4/2004 | Lloyd |
| 2004/0111050 A1 | 6/2004 | Smedley et al. |
| 2004/0116794 A1 | 6/2004 | Fink |
| 2004/0147871 A1* | 7/2004 | Burnett ............. A61M 5/14276 |
| | | | 604/9 |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0049578 A1 | 3/2005 | Tu et al. |
| 2005/0159660 A1 | 7/2005 | Montegrande |
| 2005/0271704 A1 | 12/2005 | Tu et al. |
| 2005/0273033 A1 | 12/2005 | Grahn |
| 2006/0131350 A1 | 6/2006 | Schechter |
| 2007/0019156 A1 | 1/2007 | Fink |
| 2007/0032757 A1 | 2/2007 | Medow et al. |
| 2007/0077270 A1 | 4/2007 | Wen |
| 2007/0106199 A1 | 5/2007 | Krivoy |
| 2007/0109117 A1 | 5/2007 | Heitzmann et al. |
| 2007/0123767 A1 | 5/2007 | Montegrande |
| 2007/0129623 A1 | 6/2007 | Fleischman |
| 2007/0212397 A1 | 9/2007 | Roth |
| 2008/0015421 A1 | 1/2008 | Penner |
| 2008/0027478 A1 | 1/2008 | Connors |
| 2008/0077127 A1 | 3/2008 | Gao et al. |
| 2008/0097276 A1 | 4/2008 | Bertrand et al. |
| 2008/0125691 A1 | 5/2008 | Yaron |
| 2008/0129486 A1 | 6/2008 | Jeckelmann et al. |
| 2008/0147021 A1 | 6/2008 | Jani |
| 2008/0228127 A1 | 9/2008 | Burns |
| 2009/0069648 A1 | 3/2009 | Irazoqui et al. |
| 2009/0076367 A1 | 3/2009 | Sit |
| 2009/0143713 A1 | 6/2009 | Van Dam et al. |
| 2009/0227933 A1 | 9/2009 | Karageozian |
| 2009/0240215 A1 | 9/2009 | Humayun et al. |
| 2009/0275924 A1 | 11/2009 | Lattanzio |
| 2009/0312742 A1 | 12/2009 | Pang |
| 2010/0010416 A1 | 1/2010 | Boyd |
| 2010/0042209 A1 | 2/2010 | Guarnieri |
| 2010/0121248 A1 | 5/2010 | Van Der Burg et al. |
| 2010/0174272 A1 | 7/2010 | Weiner |
| 2010/0222769 A1 | 9/2010 | Meng et al. |
| 2010/0234717 A1 | 9/2010 | Wismer |
| 2010/0253167 A1 | 10/2010 | Charnley et al. |
| 2010/0305550 A1 | 12/2010 | Meng et al. |
| 2011/0046536 A1 | 2/2011 | Stegmann |
| 2011/0071454 A1 | 3/2011 | Dos Santos |
| 2011/0071456 A1 | 3/2011 | Rickard |
| 2011/0071458 A1 | 3/2011 | Rickard |
| 2011/0071459 A1* | 3/2011 | Rickard ............. A61F 9/00781 |
| | | | 604/9 |
| 2011/0071505 A1 | 3/2011 | Rickard et al. |
| 2011/0192473 A1 | 8/2011 | Meinig et al. |
| 2011/0248671 A1 | 10/2011 | Santos et al. |
| 2012/0302861 A1* | 11/2012 | Marshall ............. A61B 5/0031 |
| | | | 600/398 |

FOREIGN PATENT DOCUMENTS

| | | |
|---|---|---|
| WO | 9803665 A1 | 1/1998 |
| WO | 9803809 A1 | 1/1998 |
| WO | 9926567 A1 | 6/1999 |
| WO | 9938470 A2 | 8/1999 |
| WO | 9938470 A3 | 10/1999 |
| WO | 9962586 A1 | 12/1999 |
| WO | 0194784 A1 | 12/2001 |
| WO | 2002056758 A1 | 7/2002 |
| WO | 03001991 A1 | 1/2003 |
| WO | 03102632 A2 | 12/2003 |
| WO | 2004073552 A2 | 9/2004 |
| WO | 2005088417 A1 | 9/2005 |
| WO | 2007087061 A2 | 8/2007 |
| WO | 2007127305 A2 | 11/2007 |
| WO | 2007136993 A1 | 11/2007 |
| WO | 2008005873 A2 | 1/2008 |
| WO | 2008061043 A2 | 5/2008 |
| WO | 2008084350 A2 | 7/2008 |
| WO | 2008061043 A3 | 9/2008 |
| WO | 2009010799 A2 | 1/2009 |
| WO | 2009026499 A1 | 2/2009 |
| WO | 2009049686 A1 | 4/2009 |
| WO | 2009081031 A3 | 9/2009 |
| WO | 2009137785 A2 | 11/2009 |
| WO | 2010129446 A1 | 11/2010 |
| WO | 2011034727 A1 | 3/2011 |
| WO | 2011034738 A1 | 3/2011 |
| WO | 2011034740 A1 | 3/2011 |
| WO | 2011034742 A2 | 3/2011 |
| WO | 2011035218 A1 | 3/2011 |
| WO | 2011034742 A3 | 5/2011 |
| WO | 2012012017 A1 | 1/2012 |

OTHER PUBLICATIONS

Bae et al., In vitro experiment of the pressure regulating valve for a glaucoma implant, J. Micromech. Microeng. 13 (2003) 613-619.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glucoma Impact"; Journal of Micromechanics and Microengineering, 13 (2003); pp. 613-619.

(56) References Cited

OTHER PUBLICATIONS

Driot et al.; "Ocular pharmacokinetics of fluocinolone acetonide after RetisertTM intravitreal implantation in rabbits over a 1-year period"; J. Ocular Pharm; 20; 3; pp. 269-275.
Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.
Erik Stemme and Goran Stemme; "A Valveless Diffuser/Nozzle-Based Fluid Pump"; ScienceDirect; Sensors and Actuators A, 39 (1993); pp. 159-167.
Glybina et al; "Neuroprotective properties of fluocinolone acetonide chronically delivered into the vitreous of albino RCS rats"; IVOS; 47; ARVO e-Abstract 1028.
Greene, M.E. And Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.
Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.
Kuppermann B D et al., 2006, "Efficacy and safety of a novel intravitreous dexamethasone drug-delivery system after applicator or incisional placement in patients with macular edema", IOVS, 47 ARVO E-Abs 5913.
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring,"In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol.45, No.9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Miyamoto H et al., 1997, Biodegradable scleral implant for intravitreal controlled release of fluconazole, Curr Eye Res, 16(9), 930-935.
Mokwa, Wilfried, et al, "Micro-Transponder Systems for Medical Applications," IEEE Transactions on instrumentation and Measurement, Dec. 2001, pp. 1551-1555, vol. 50, No. 6, IEEE, Germany.
Mruthyunjaya P. et al., 2003, "An intravitreal sustained release fluocinolone acetonide device to treat severe experimental uveitis", IOVS, 44, ARVO E-Abs 4215.
Neagu Cristina R.; "A Medical Microactuator Based on an Electrochemical Principle"; Thesis at the Twente University, the Netherlands, Enschede; Aug. 28, 1998; pp. 1-162.
Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.
Puers, Robert, "Linking Sensors with Telemetry: Impact on the System Design," in Proc. 8th Int'l Conference of Solid State Sensors, Actuators, Eurosens, Jun 25-29, 1995, pp. 169-174, Stockholm, Sweden.
Ratanapakorn T et al., 2005, "Helical intravitreal triamcinolone implant: An explanation survival study", IVOS 46 E-Abs 484.
Rego MGR et al., 2004, "In vitro evaluation of sustained-release intravitreal dexamethasone implants", IOVS, 45 E-Abs 5060.
Sakurai E et al., 2001, "Scleral plug of biodegradable polymers containing ganciclovir for experimental cytomegalovirus retinitis", IOVS, 42(9), 2043-2048.
Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; Pgs. 60-71.
Schnakenberg, U., et al, "Initial Investigations on Systems for Measuring Intraocular Pressure," Sensors and Actuators, 2000, pp. 287-291, vol. 85, Elsevier Science B.V., Germany.
See R F et al., 2006, "Safety and drug release profile of injectable intravitreal sustained-release fluocinolone acetonide device", IOVS, 47, ARVO E-Abs 5119.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Sutanto, et al., Design, microfabrication and testing of a CMOS compatible bistable electromagnetic microvalve with latching/unlatching mechanism on a single wafer, J. Micromech. Micromeng. 16 (2006) 266-275.
Tano R et al., 2005, Helical intravitreal implant: surgical method development and outcomes, IOVS, 46, ARVO E-Abs 483.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Varner S E et al., 2003, "Development of a minimally invasive intravitreal implant for drug delivery", IOVS, 44, ARVO E-Abs 4214.
Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue Volume 240, Number 5/May, 2002 DOI 10.1007/s00417-002-0474-y; pp. 335-336; Subject Collection Medicine.
Weiner A L, 2007, "Drug Delivery Systems in Ophthalmic Applications, in: Ocular Therapeutics; Eye on New Discoveries; T. Yorio, A. Clark, M.Wax, Eds, Elsevier Press/Academic Press, New York", pp. 7-43.
Yasukawa T et al., 2001, "Biodegradable scleral plugs for vitreoretinal drug delivery", Adv. Drug Del Rev., 52(1), 25-36.

* cited by examiner

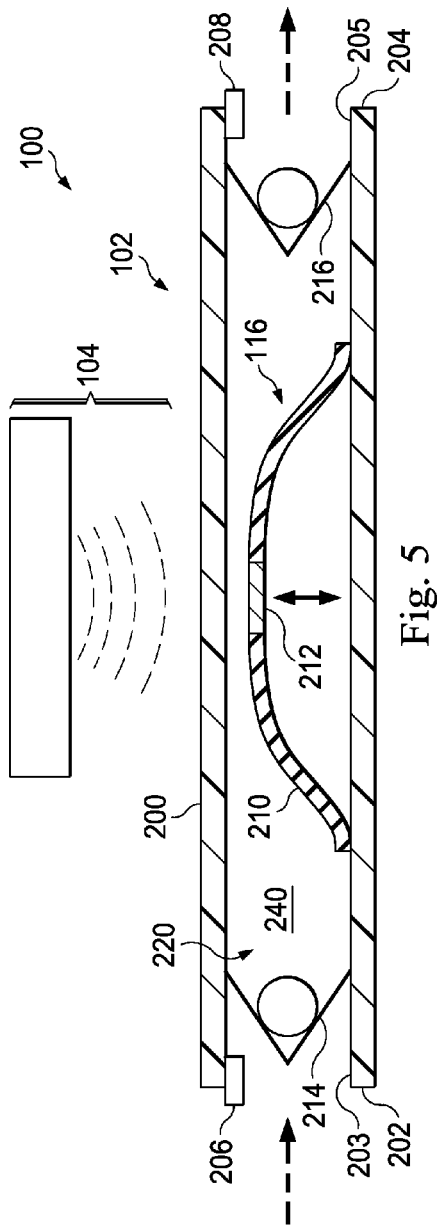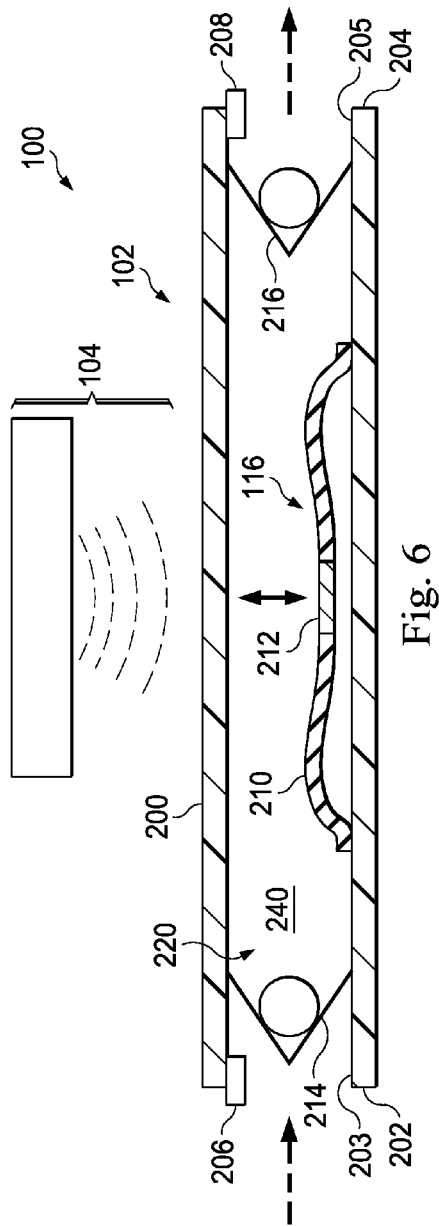

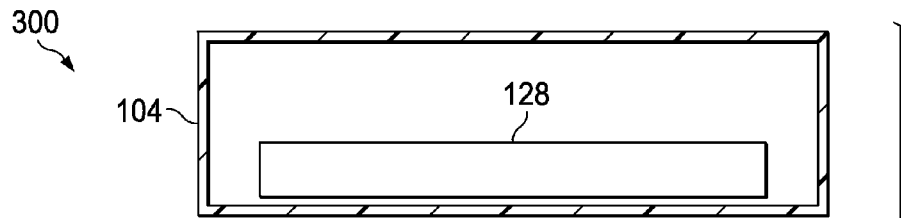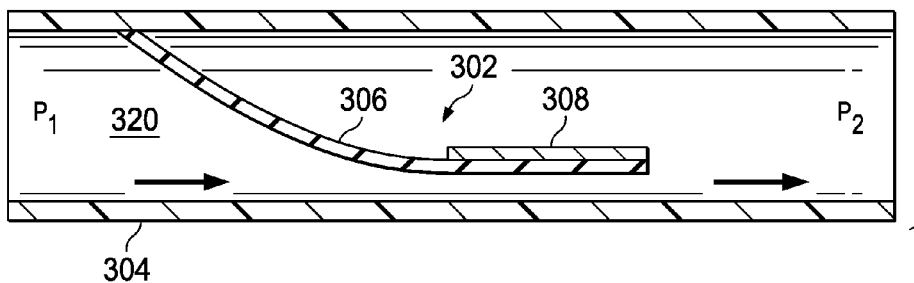
Fig. 7
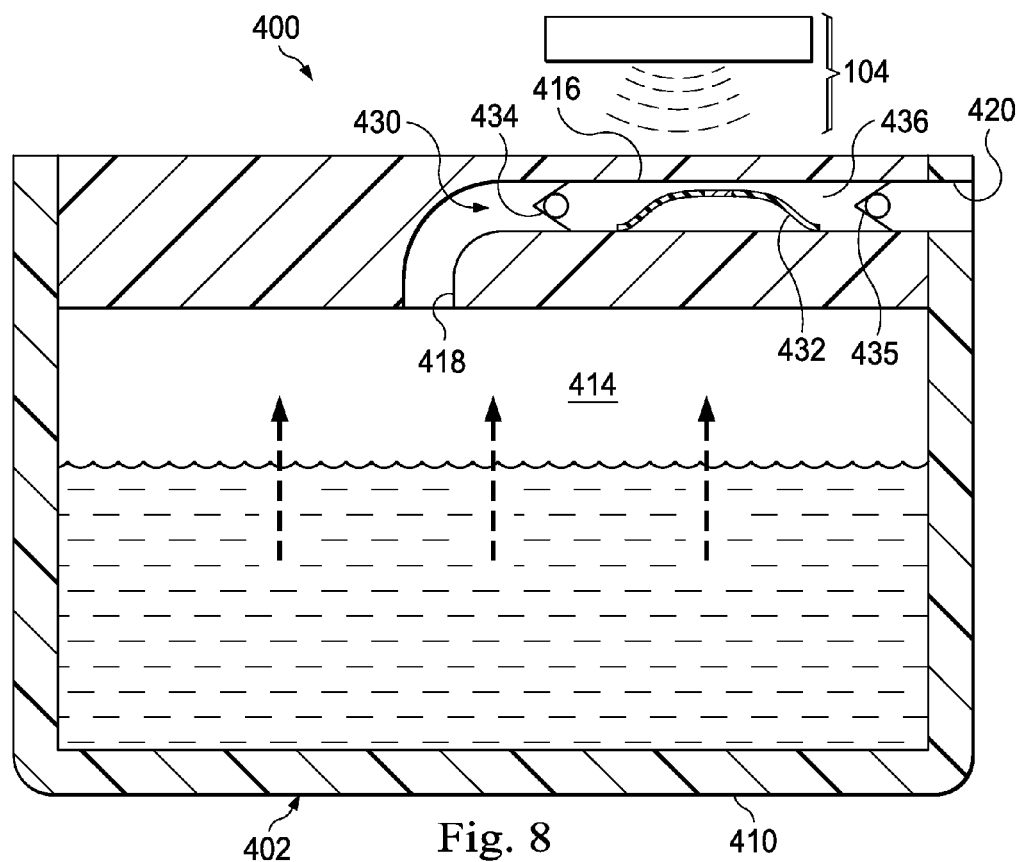
Fig. 8

REMOTE MAGNETIC DRIVEN FLOW SYSTEM

FIELD OF THE INVENTION

The present disclosure relates generally to flow control systems for ocular implants and drug delivery devices. More particularly, but not by way of limitation, the present disclosure pertains to a remotely, magnetic driven flow control system.

BACKGROUND

Glaucoma, a group of eye diseases affecting the retina and optic nerve, is one of the leading causes of blindness worldwide. Most forms of glaucoma result when the IOP increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 10, cornea 20, iris 30, ciliary body 40, trabecular meshwork 50, and Schlemm's canal 60 are pictured. Anatomically, the anterior segment of the eye includes the structures that cause elevated IOP which may lead to glaucoma. Aqueous humor fluid is produced by the ciliary body 40 that lies beneath the iris 30 and adjacent to the lens 10 in the anterior segment of the eye. This aqueous humor washes over the lens 10 and iris 30 and flows to the drainage system located in the angle of the anterior chamber 70. The angle of the anterior chamber 70, which extends circumferentially around the eye, contains structures that allow the aqueous humor to drain. The trabecular meshwork 50 is commonly implicated in glaucoma. The trabecular meshwork 50 extends circumferentially around the anterior chamber. The trabecular meshwork 50 may act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber. The two arrows in the anterior segment of FIG. 1 show the flow of aqueous humor from the ciliary bodies 40, over the lens 10, over the iris 30, through the trabecular meshwork 50, and into Schlemm's canal 60 and its collector channels.

One method of treating glaucoma includes implanting a drainage device in a patient's eye. The drainage device allows fluid to flow from the anterior chamber of the eye to a drainage site, relieving pressure in the eye and thus lowering IOP. These devices are generally passive devices that do not provide a smart, interactive control of the amount of flow through the drainage tube. Once the drainage device is implanted, the body may form a bleb, or fluid-filled space surrounded by scar tissue, at the drainage site into which aqueous humor flows via a drainage tube. Changes at the drainage site such as scar tissue formation may affect the pressure differentials acting on the drainage device, thereby affecting the passive flow through the device. In order to provide desired treatments to patients, it may be important to actively regulate the flow of aqueous humor through the drainage device into the drainage site.

The system and methods disclosed herein overcome one or more of the deficiencies of the prior art.

SUMMARY

In an exemplary aspect, the present disclosure is directed to a system for implantation in an eye of a patient and includes a flow device sized for implantation into the eye of the patient, the flow device including a housing with an inlet port and an outlet port, including a fluid flow passageway extending through the housing from the inlet port to the outlet port to allow the flow of fluid from the inlet port to the outlet port, and including a flow system disposed within the flow device. The flow system may include a regulator having a magnetic element, and may be displaceable in the fluid flow passageway to affect flow through the fluid flow passageway. The system may also include a control device physically separate from the flow device and configured to be disposed outside the eye, the control device comprising an actuator magnetic field generator configured to act on the magnetic element to adjust the regulator in the flow system to selectively adjust flow through the flow device in response to changes in intraocular pressure.

In some aspects, the control device comprises an eyeglass frame. In some aspects, the control device comprises a wearable article that may be, for example, a hat or a headband. In some aspects, the regulator includes a portion formed in the shape of an arch in cross-section, the magnetic element being disposed on the arch in a location that the arch displaces in a direction transverse to the flow direction in order to selectively restrict and allow fluid flow. In some aspects, the regulator is a flexible membrane portion and is configured to flex and move through the fluid flow passageway in the direction of the actuator when subjected to a magnetic field. In some aspects, the flow system includes a first one-way valve disposed upstream from the regulator in the fluid flow passageway, and a second one-way valve disposed downstream from the regulator in the fluid flow passageway, the regulator being actuatable to create a pumping effect with the first and second one-way valves. In an aspect, the control device comprises a power source larger than the flow device, the power source being configured to power the magnetic field generator. In an aspect, the control device comprises: a first sensor configured to detect pressure representative of pressure in an anterior chamber of the eye; and a second sensor configured to detect pressure representative of pressure in the drainage site. In an aspect, the control device emits RF transmissions and wherein the flow device harvests power from the transmissions to power the first and second sensors.

In an exemplary aspect, the present disclosure is directed to an implantable fluid flow system that includes a housing including an inlet port and an outlet port and a reservoir for maintaining a drug. A fluid flow passageway extends through the housing from the inlet port to the outlet port to allow the flow of fluid from the inlet port to the outlet port. A flow system is disposed within the housing and includes a regulator displaceable in the fluid flow passageway to affect flow through the fluid flow passageway. A control device is disposed physically separate from the housing and configured to be disposed outside the patient. The control device includes a magnetic field generator configured to adjust the regulator in the flow system to selectively adjust flow through the housing.

In an exemplary aspect, the present disclosure is directed to a method of regulating fluid flow from an anterior chamber of an eye. The method includes directing fluid through an implantable flow device including a housing defining a fluid flow passageway and including a flow system comprising a regulator responsive to a control device physically separate from the flow device and configured to be disposed outside the eye to adjust flow through the fluid flow passageway, and modifying the amount of drainage through the implantable flow device by creating a magnetic field with the control device.

In some aspects, modifying the amount of drainage through the implantable flow device comprises activating an actuator to adjust the regulator to affect flow through the fluid flow passageway. In some aspects, modifying the amount of drainage through the implantable flow device comprises activating the actuator in response to the intraocular pressure exceeding a predetermined threshold. In some aspects, modifying the amount of drainage through the implantable flow device comprises activating the actuator to change the position of the sealing portion in the fluid flow passageway relative to the housing.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 5 is a stylized illustration of a cross-sectional view of an exemplary drainage device according to the principles of the present disclosure, showing the exemplary flow system in a more closed condition.

FIG. 6 is a stylized illustration of a cross-sectional view of an exemplary drainage device according to the principles of the present disclosure, showing the exemplary flow system in a more open condition.

FIG. 7 is a stylized illustration of a cross-sectional view of another embodiment of an exemplary drainage device according to the principles of the present disclosure.

FIG. 8 is a stylized illustration of a cross-sectional view of an exemplary drug delivery device incorporating the principles of the present disclosure.

DETAILED DESCRIPTION

Figure 1:
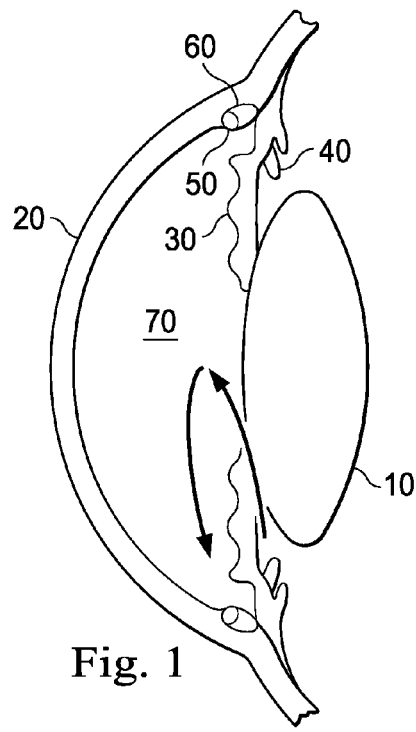
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to fluid flow systems that may find particularly utility as a part of an IOP control system arranged to regulate flow from an anterior chamber of the eye to a drainage site and as a part of a drug delivery device. In embodiments where the fluid flow system is a part of an IOP control system, the flow system may form a part of a glaucoma drainage device (GDD) implantable in an eye. In embodiments where the fluid flow system is a part of a drug delivery device, the flow system may be implanted as a part of the device in the eye or elsewhere for delivery of a particular volume of a drug to treat a condition. The fluid flow systems may be regulated via a remote, non-implanted external device that actuates the flow system as a pumping device to control dosage through the devices.

Drainage devices which rely on the pressure differential between the anterior chamber and the drainage site may cause a detrimental hypotonous state by releasing aqueous humor too fast from the anterior chamber after the initial implantation. It is not until a few weeks after implantation that a bleb forms at the drainage site to sufficiently regulate the fluid flow. In addition, progressive scarring of the bleb over time may cause the bleb pressure to increase, resulting in an increase in IOP. Flow systems that rely solely on the pressure differential between the anterior chamber and the drainage site to create flow through the device may eventually fail due to this effect, by increasing the IOP above an acceptable threshold which varies from patient to patient (e.g., 12 mmHg).

The systems disclosed herein find particular utility when regulating fluid flow through a GDD after implantation in the early stages when pressure differential between the anterior chamber and the drainage site may be high, and later when pressure differentials between the anterior chamber and the drainage site are lower and do not permit passive fluid flow at the flow rates desired. Such systems may treat glaucoma as described above. FIGS. 2-7 describe systems that may be used for such ocular treatments.

Figure 2:
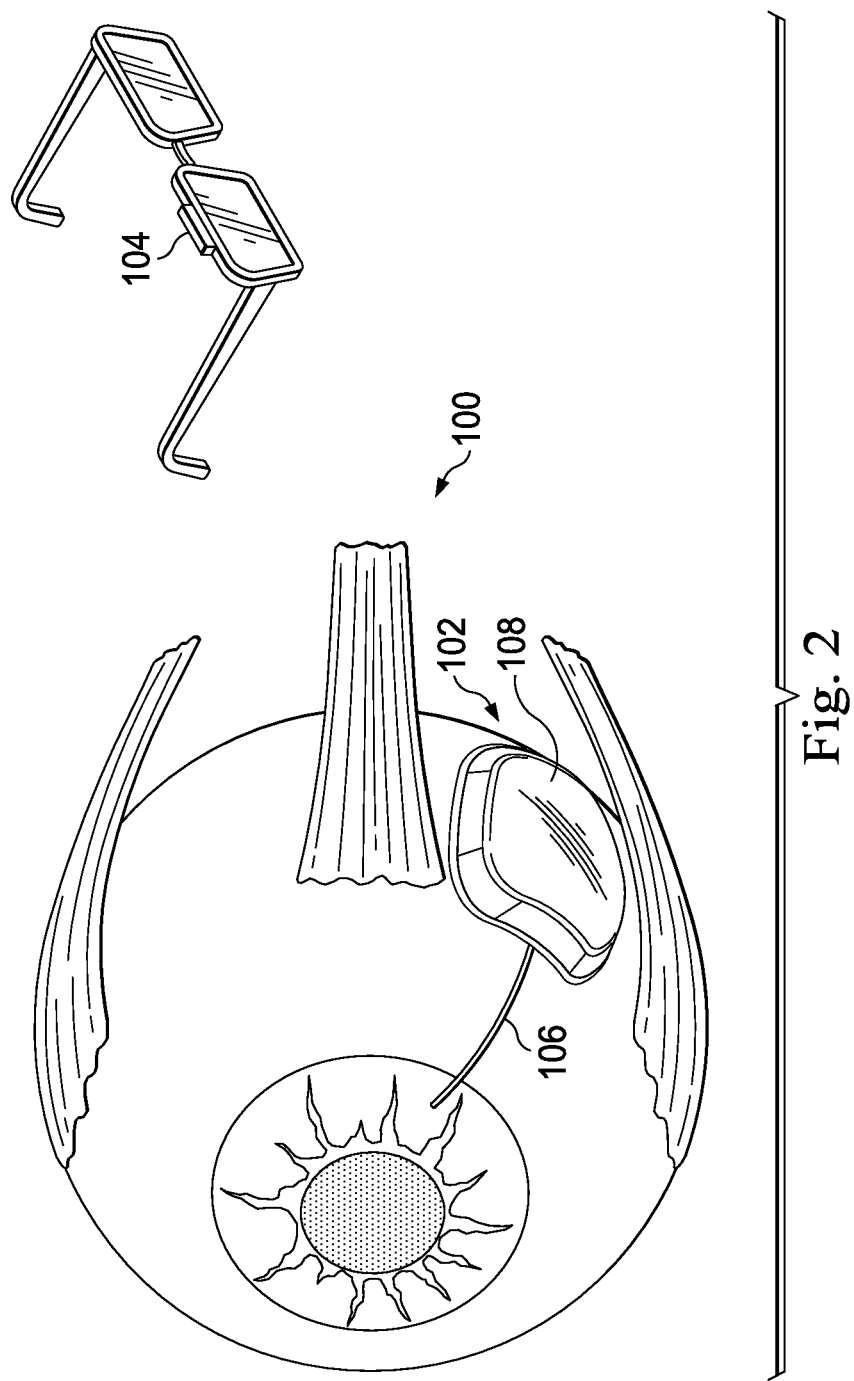
FIG. 2 is an illustration of an exemplary IOP control system according to the principles of the present disclosure.

FIG. 2 is a schematic partial block diagram of an exemplary IOP control system 100 usable for the treatment of glaucoma or other ocular conditions according to the principles of the present disclosure. In FIG. 2, the IOP control system 100 comprises an implantable drainage device 102 implanted on or within an eye and a control device 104 separate from and spaced from the drainage device 102 and the eye. The drainage device 102 is designed to open when pressure in the anterior chamber is greater than, or exceeds a threshold value of, the pressure at a drainage site in the eye.

Conventionally, after a pressure-driven passive drainage device is implanted within the eye, IOP tends to fall rapidly as aqueous fluid flows immediately through the drainage device to a drainage site. Over time, the differential in pressure at the drainage site and the pressure in the anterior chamber tends to decrease, and as such, the flow likewise decreases. However, in the embodiments disclosed herein, the drainage device 102 can be actively actuated by the control device 104 to pump drainage fluid through the device 102. Thus, the systems and devices disclosed herein may regulate flow through the drainage device even when the pressure differential between the anterior chambers is about equal to or less than the pressure at a drainage site in the eye.

In some aspects, the drainage device 102 is implanted within the eye to extend from the anterior chamber 70 (FIG. 1) to a drainage site (not shown). In some embodiments, the drainage location is from the posterior chamber. In some embodiments, the drainage site is the suprachoroidal space. In other embodiments, the drainage site may be located elsewhere, such as, by way of non-limiting example, the subconjunctival space. The drainage device 102 is configured to carry various components of the IOP control system 100, and may include, by way of non-limiting example, any number of drainage tubes, valves, pumps, transducers, or sensors. In some aspects, the drainage device 102 is configured to fit at least partially within the suprachoroidal space and is sized for example within a range between about 50 µm×50 µm to about 250 µm×250 µm. In some embodiments, the drainage device 102 has a thickness less than or equal to about 250 µm. For example, in one embodiment, the drainage device 102 has a thickness of about 250 µm. Other sizes and thicknesses are also contemplated (e.g., without limitation, up to 2.5 mm thick, with an area less than or equal to 350 mm$^2$) The drainage device 102 may be curved to approximate the radius of the eye globe. In some embodiments, the drainage device 102 is rigid and preformed with a curvature suitable to substantially conform to the globe. In other embodiments, the drainage device 102 is flexible to conform to the globe. The above dimensions and arrangement are exemplary only, and other sizes and arrangements are contemplated.

The drainage device 102 (FIG. 2) is sized to extend from the anterior chamber 70 of the eye to the drainage site in the eye, thereby bridging the anterior chamber 70 and the drainage site to provide an auxiliary flow path for aqueous humor, bypassing the flow-resistive conventional pathway through the trabecular meshwork and shunting aqueous humor directly to the drainage site. In the example shown, the drainage device 102 includes a single hollow tube 106 and a main body 108 as a housing. Other embodiments include a plurality of tubes or a plurality of lumens cooperating together to permit fluid to flow through the drainage device 102. Aqueous humor may drain through the drainage device 102 from the anterior chamber 70 to the drainage site to alleviate elevated intraocular pressure conditions. In some embodiments, the main body 108 is a tube with a lumen forming a drainage pathway.

Still referring to FIG. 2, the IOP control system 100 includes the control device 104. The control device 104 is carried off-board the implant and is configured and arranged to be spaced apart from the eye. However, it is configured to communicate with the drainage device 102 in any of multiple ways in order to provide control to the drainage device 102. In some embodiments, as is described in greater detail below, the control device 104 generates and emits an electromagnetic field, RF signals, infrared signals, or signals and fields that may be detected and received by the drainage device 102. As will be explained below, the signals, including fields, control features of the drainage device 102 in a way that allows the control device 104 to regulate fluid flow through the drainage device 102, thereby impacting or actively controlling IOP.

As described below with reference to FIG. 4, the control device 104 is arranged to carry various components of the IOP control system 100, and may include transducers or sensors, a processing system, a memory, a power source, an actuator, and/or other components that may be used to either control the drainage device 102 or otherwise treat ocular conditions. The control device 104 in FIG. 2 is spaced from the eye and is in wireless communication with the drainage device 102. In some examples, it is maintained within the proximate area of the eye in order to communicate with the drainage device 102 in the manner discussed above. In some embodiments, the control device 104 is carried on items wearable by the user, such as on a pair of eyeglasses, a hat, headband, jewelry, or other wearable item. FIG. 2 shows the control device disposed upon a frame of eyeglasses. Accordingly, a user may wear the eyeglasses which may maintain the control device 104 in close proximity to the eye so that treatment via the drainage device 102 may be ongoing as needed or as desired. The control device 104 may include other elements that may be connected via wire or through a wireless communication system that may permit at least some components, such as a power source, to be carried off the wearable article, such as in a pocket.

Figure 3:
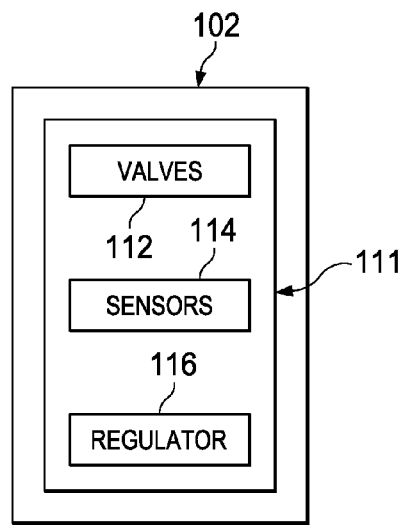
FIG. 3 is a block diagram of an exemplary implantable drainage device in accordance with embodiments of the present disclosure.
Figure 4:
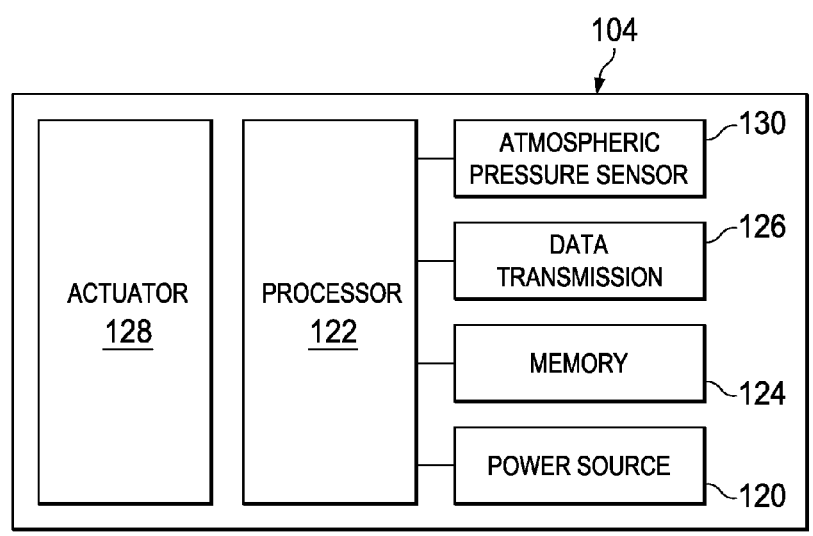
FIG. 4 is a block diagram of an exemplary control device in accordance with embodiments of the present disclosure.

FIGS. 3 and 4 are block diagrams showing the drainage device 102 and the control device 104, respectively. Referring to FIG. 3, the drainage device 102 includes a flow system 111 that may include any of a plurality of different flow regulating elements, and in the embodiment shown, the flow system 111 includes one or more valves 112, one or more sensors 114, and one or more regulators 116. As will be described below, the components of the flow system 111 may together form one or more pumps, processing elements, or other elements. These may be arranged in a manner that regulates the drainage fluid flow through the drainage device, from the anterior chamber to the drainage site. The valves 112 may be disposed along the fluid flow pathway through the drainage device 102 and may help regulate flow through the device 102. In some embodiments, the valves 112 are one-way valves that permit fluid only in the drainage direction, adjustable flow control valves, and/or on-off valves. Other valves may also be used. The valves 112 may be controlled via signals from the control device 104 or may be passive check valves that permit fluid in the direction of the flow toward the drainage site.

The sensors 114 are configured to measure conditions of the patient or the drainage device. In some embodiments, the sensors 114 are configured and disposed to measure physiologically conditions of the patient. Accordingly, the sensors may be configured to measure the pressure of the anterior chamber and/or pressure of the drainage site. The sensors 114 may also measure other conditions, such as temperature, drainage flow rates, or other conditions. The sensors 114 may also measure pressure in chambers of the drainage device 102, valve settings, or other measurable parameters. Information obtained from the sensors may be wirelessly communicated to the control device 104.

The regulator 116 controls the fluid flow through the drainage device and cooperates with the valves 112 to create a pump to regulate and control flow through the drainage device 102. The regulator 116 may be a valve or may be some other flow regulator that adjusts to increase and decrease the flow of fluid through the drainage device 102. Some examples of regulators will be described further below.

Turning now to FIG. 4, the control device 104 may comprise any of a variety of component parts, including, by way of non-limiting example, a power source 120, a processor 122, a memory 124, a data transmission module 126, an actuator 128, and an atmospheric pressure sensor 130. Additional components may be included, while in some embodiments, the control device 104 lacks some of these components. For example, in some embodiments, the control device 104 comprises only an actuator 128. In one embodiment, the actuator 128 is configured to actuate the regulator 116 within the drainage device 102.

The power source 120 may be, for example, a rechargeable battery, such as a lithium ion or lithium polymer battery, although other types of batteries may be employed. In other embodiments, any other type of power cell is appropriate for the power source 120. The power source 120 provides power to the control device 104, and may be configured to power the actuator, which in turn may wirelessly actuate or otherwise power the valves 112, sensors 114, or regulator 116 on the drainage device 102. In some examples, sufficient power is provided through on-board batteries and/or wireless powering.

The processor 122 may be an integrated circuit with power, input, and output pins capable of performing logic functions. For example, the processor 122 may perform logic functions based on inputs from the atmospheric pressure sensor 130 and the sensors 114 on the drainage device to determine the current IOP of the eye and/or the operating status of the IOP control system 100 (note, the IOP is the difference between the anterior chamber pressure and the atmospheric pressure). In some embodiments, the processor 122 controls the supply of power from the power source 120 to the drainage device 102 and/or signal commands to the drainage device 102. In various embodiments, the processor 122 may be a targeted device controller or a microprocessor configured to control more than one component of the drainage device 102 or a combination thereof. The processor 122 may include one or more programmable processor units running programmable code instructions using the actuator 128 to control the drainage device 102 to provide a desired IOP or otherwise regulate flow through the drainage device, among other functions.

In some embodiments, the processor 122 is selectively coupled to a computer and/or other types of processor-based devices suitable for a variety of ocular applications. In various embodiments, the processor 122 can receive input data from a user, the atmospheric pressure sensor 130, the drainage device 102, and/or various accessory devices via wireless or wired mechanisms. The processor 122 may use such input data to generate control signals to control or direct the operation of the drainage device 102. In some embodiments, the user can regulate or direct the operation of the drainage device 102 through the control device 104.

The memory 124, which is typically a semiconductor memory such as RAM, FRAM, or flash memory, interfaces with the processor 122. As such, the processor 122 can write to and read from the memory 124, and perform other common functions associated with managing semiconductor memory. For example, a series of pressure readings, IOP calculations, and/or command sequences can be stored in the memory 124.

The processor 122 and/or the memory 124 may also include software containing one or more algorithms defining one or more functions or relationships between command signals and input data (received from the drainage device 102 and/or accessory devices). The algorithm may dictate activation or deactivation command protocols/signals (e.g., to the actuator 128) depending on the received input data or mathematical derivatives thereof. In some embodiments, the algorithm may dictate activation or deactivation control signals affecting particular valves 112 or the regulator 116 on the drainage device 102 when the input data indicates an IOP below a predetermined threshold value, above a predetermined threshold value, and/or when the input data indicates a specific physiologic event, temporal state, or pathologic condition (e.g., hypotony, bleb scarring, or an initial post-operative state). The processor 122 may be configured to selectively implement one or more control algorithms to enable IOP control. In some embodiments, the processor 122 may be re-programmed to selectively implement one or more particular control algorithms.

In various embodiments, the control device 104 may be operatively coupled to the drainage device 102 by wireless communication mechanisms. In some embodiments, the external IOP control device 104 may affect the drainage device 102 by utilizing wireless communication between the drainage device 102 and the secondary control device 104. Contemplated wireless communication methods include, by way of no limiting example, cooperating transmitters and receivers positioned on various components of the IOP control system 100 to allow remote communication between various components of the system 100.

Thus, the data transmission module 126 may employ any of a number of different types of data transmission. For example, in various embodiments, the data transmission module 126 may be an active device such as a radio or a passive device with an antenna capable of wireless communication. In some embodiments, the data transmission module 126 may be activated to communicate the open and closed status of individual valves 112, the status of the regulator 116, and/or data from the sensors 114 from the drainage device 102 to the secondary control device 104 or other electronic device or service such as, by way of non-limiting example, a PDA, cell phone, computer, remote accessible data storage site (e.g., an internet server, email server, or text message server). In some embodiments, control signals or program algorithms may be transmitted to the data transmission module 126 from an external device to adjust the treatment settings.

The actuator 128 is configured to influence the valves 112, sensors 114, and/or regulator 116 within the drainage device 102. Some valves are passive valves and are not controlled by the actuator 128, and other valves are actively controlled. In one embodiment, the actuator is a magnetic field generator. For example, the actuator 128 is configured to selectively open the valves 112 to increase flow through the drainage device 102. In some embodiments, the actuator 128 can selectively open individual valves of the valves 112 or control the regulator 116 independently of each other. In some embodiments, the actuator 128 comprises an electromagnet configured to selectively open and close individual valves 112 within a flow system (described below) of the drainage device 102. In some embodiments, the actuator 128 can act upon the drainage device 102 without the use of the processor 122. In other embodiments, the actuator 128 is controlled by the processor 122.

The atmospheric pressure sensor 130 is carried on the control device and detects atmospheric pressure. Data obtained from the pressure sensor 130 may be used, together with information from the sensors 114 on the drainage device 102, to determine IOP of the eye. Based on the IOP, the processor 122 may control the actuator 128 to control the valves 112 and the regulator 116 to increase, decrease, or maintain IOP at a desired level.

FIG. 5 is a schematic diagram of the IOP control system 100 showing a portion of the drainage device 102 and the control device 104. In use, the drainage device 102 is implanted in an eye of a patient for the treatment of glaucoma or other ocular conditions. The control device 104 is not implanted on the patient, but is maintained apart from, and is in communication with the drainage device 102. Here, the drainage device 102 is shown as a tube or a portion of a tube that is arranged to drain fluid from the anterior chamber 70 (FIG. 1) to the drainage site.

Since the power source for the IOP control system 100 is maintained as a part of the control system 104, which is separate and apart from the implanted drainage device 102, the drainage device 102 may be sized smaller, be more compact, weigh less, and be otherwise more comfortable and less obtrusive than when a drainage device carries a power source. In addition, since the power source is not limited to a size that is implantable in the eye, the power source in the IOP control system 100 may be larger and configured to provide high power levels that may not be attainable by power sources on a drainage device that fits within the eye. Accordingly, because of the higher obtainable power levels, transmission distances may be greater than when power sources are disposed on implanted ocular devices.

In the embodiment pictured in FIG. 5, the drainage device 102 includes a housing as a drainage tube 200, valves 214, 216 (corresponding to the valves 112 in FIG. 3), sensors 206, 208 (corresponding to the sensors 114 in FIG. 3), and a regulator 116. These may be disposed along the drainage tube 200 between a proximal end 202 with an inlet port 203 of the drainage tube 200 in the anterior chamber 70 and a distal end 204 with an outlet port 205 of the drainage tube 200, which leads to the drainage site. The drainage tube 200 drains aqueous humor from the anterior chamber 70 of the eye to the drainage site. The valves 214, 216 and regulator 116 control the flow of aqueous humor through the drainage tube 200. In the exemplary embodiment shown, the valves 214, 216 are comprised of two passive one-way check valves. Other embodiments include active valves that may be controlled by the control device 104.

The regulator 116 is disposed to cooperate with the drainage tube 200 between the valves 214, 216. In this embodiment, the regulator 116 is a flexible portion 210 with a magnetic element 212 disposed thereon. The flexible portion 210 is configured to displace due to a magnetic field generated on the external device acting on the magnetic element 212. The magnetic element 212 may be a metal that may be affixed onto or may form a part of the flexible portion 210. Accordingly, when the magnetic element moves, the flexible portion also moves.

As the flexible portion 210 displaces within the drainage tube 200, the cross-sectional area of the flow path through the drainage tube 200 decreases, thereby decreasing the amount of fluid passing the flexible portion and likewise decreasing flow. As the flexible portion 210 displaces to increase the cross-sectional area of the flow path, the resultant flow increases.

The flexible portion 210 may be formed of an elastically deformable biocompatible material such as, by way of non-limiting example, silicone, silicon nitride, silicone elastomer, polyimide, Parylene, and others. In the example shown, the flexible portion 210 is shaped as a flexible membrane that is secured at its periphery to the flow tube 200.

The sensors 206, 208 are disposed along the drainage device in locations to measure distinct pressure zones. In FIG. 5, a sensor 206 is disposed along an anterior side toward the distal end 202 of the drainage device 102 and a sensor 208 is disposed along the drainage side toward the proximal end of the drainage device 102. As such, the sensor 206 may be disposed and arranged to measure or detect pressure indicative of the anterior chamber of the eye and the sensor 208 may be disposed and arranged to measure or detect pressure indicative of the drainage side of the eye. The difference between the pressures detected by sensors 206, 208 provides an indication of the pressure differential across the drainage device 102 or a portion of the drainage device 102 (e.g., between the anterior chamber 70 and the drainage site). This pressure differential may dictate the rate of aqueous humor flow from the anterior chamber 70 to the drainage site.

Generally, IOP is a gauge pressure reading—the difference between the absolute pressure in the eye (e.g., as measured by the anterior chamber pressure sensor 206) and atmospheric pressure (e.g., as measured by the atmospheric pressure sensor 130 on the control device 104). In some embodiments, pressure readings are taken by the sensors 206, 208, 130 simultaneously or nearly simultaneously over time so that the actual IOP can be determined Pressure measurements by any pressure sensors 206, 208, 130 may be stored in a memory such as, by way of non-limiting example, the memory 124 by the processor 122. They can later be read from the memory source so that the pressure drop across the drainage device 102 over time can be interpreted by a user, such as a patient or a healthcare professional.

As indicated with respect to FIG. 3, the valves 112 and the regulator 116 form the flow control system 111 and are configured to control the flow of drainage fluid through the drainage tube 200, and thereby affect pressure in the eye, including the IOP. In FIG. 5, the valves 214, 216, and the regulator 116 form a flow system 220. A desired pressure differential can be maintained by controlling the flow through the drainage tube 200 with the flow system 220. For example, when the IOP is too high, the flow system 220 may operate to permit increased flow through the drainage tube 200, and when the IOP is too low (e.g., in a hypotonous state where aqueous humor is draining too rapidly from the anterior chamber), the flow system 220 may operate to decrease the flow through the drainage tube 200. Likewise, some embodiments of the IOP control system 100 are configured to control the flow of drainage fluid to the drainage site (e.g., a bleb), and thereby control the bleb pressure to maintain a desired fluid flow to the bleb, decrease fibrosis, and increase absorption efficiency. To accomplish this, the flow system 220 may be responsive to the control device 104 based on input data received from the atmospheric pressure sensor 130, the sensors 114, 206, 208, IOP calculations, and/or a pre-programmed treatment protocol (e.g., based on the current IOP or the time lapse after initial implantation). Such a treatment protocol may be stored in the memory 124 (shown in FIG. 4).

FIG. 5 shows the IOP control system 100 when the regulator 116 is disposed in a manner limiting flow through drainage device 102, and FIG. 6 shows the IOP control system 100 when the regulator 116 is disposed in a manner that allows increased flow through the drainage device 102. In some embodiments, the regulator 116 is biased to a position that either limits flow, as when the regulator blocks more than one-half of the cross-sectional area of the flow tube, or allows higher flow, as when the regulator blocks less than one-half of the cross-sectional area of the flow tube. The regulator 116 displaces when subjected to the magnetic field generated by the control device 104 that is spaced apart from and carried outside the eye.

The regulator 116 moves between the higher flow position and the lower flow position in FIGS. 5 and 6, and may be configured to entirely prevent or restrict flow in some instances. In an exemplary embodiment, when the control device 104 is actuated or under power, it may attract or repel the magnetic element 212. In addition, since the regulator 116 is biased to a particular position, the absence of the magnetic field also impacts the flow as the regulator 116 returns to its predisposed position. Depending on the embodiment, the activation of the actuator 128 adjusts (e.g., by way of non-limiting example, expands, contracts, rotates, or moves) the magnetic element 212 to displace the flexible portion 210.

In some embodiments, the regulator 116 and valves 112 cooperate to create a pump in the flow system 220 in the drainage tube 200. That is, the portion of the drainage tube between the two check valves 214, 216 forms a pump chamber 240, and the regulator 116 is disposed within the pump chamber. In response to a magnetic field generated by the control device 104, the regulator 116 moves to a more open position as shown in FIG. 6. This may create a vacuum in the chamber 240 that draws fluid into the chamber through the check valve 214 from the anterior chamber of the eye. In response to an opposite magnetic field generated by the control device 104, the regulator 116 moves to a more closed position as shown in FIG. 5. This may increase the fluid pressure in the chamber until the fluid is forced from the chamber 240 through the check valve 216 toward the drainage site.

FIG. 7 shows a stylized cross-sectional view of another embodiment of an exemplary IOP control system with a flow system 300. The device in FIG. 7 has many of the same or similar elements as those disclosed with reference to FIGS. 5 and 6. However, this embodiment includes a regulator 302 formed as a flap valve or flexible cantilever valve in a housing 304. The regulator 302 includes a flexible portion 306 and a magnetic element 308. The regulator 302 is configured as a flow control valve that can completely or partially block the flow of aqueous humor by deflecting the flexible portion 306 completely or partially across a fluid flow passageway 320. The flexible portion 306 here is a cantilever portion and the magnetic element 308 is coupled to a distal end. The magnetic element 308 is configured to be responsive to the control device 104. In some embodiments, the magnetic element 308 is configured to be responsive to the actuator 128 of the control device 104. In the pictured embodiment, the magnetic element comprises a metallic element, deposit, or strip. The magnetic element 308 may be formed of any of a variety of metallic materials that are responsive to a magnetic field. A magnetic field generated by the actuator 128 displaces or holds the flexible portion 306 in a position that controls the amount or the degree that the valve is opened or closed.

Other embodiments may include any number, type, and arrangement of valves and regulators, provided that they are capable of remote actuation via a wireless control system to selectively restrict the flow of fluid through the fluid flow passageway based on the pressure differential between the distal and proximal sides of the device. Some details of the flap valve are disclosed in U.S. Pat. No. 9,283,115, titled "Passive to Active Staged Drainage Device" incorporated herein by reference.

FIG. 8 shows a stylized drug delivery system 400 that operates on the principles discussed above. In this example, the drug delivery system 400 includes an implantable delivery device 402 and a separate, spaced apart control device 104. The delivery device 402 may form a part of the drainage device 102 or may otherwise form a part of a non-draining implant. The control device 104 may include at least some of the same features as the control device 104 discussed above. Therefore, the control device 104 will not be described in detail.

The delivery device 402 includes a housing 410 and a drug reservoir 414. A drainage tube 416 has a distal end 418 as an inlet port and a proximal end 420 as an outlet port and extends from the reservoir 414 to a medication treatment site.

The delivery device 402 also includes a flow system 430 that regulates the amount or volume of drug that flows from the drug reservoir 414 to the treatment site. The flow system 430 is similar in many respects to the flow system 430 described above, and only portions of the flow system 430 will be described since the description above applies to the flow system 430. The flow system 430 includes a regulator 432 and valves 434, 435 that cooperate to regulate flow and, here, create a pump in the drainage tube 416. The portion of the drainage tube 416 between the valves 464, 435 forms a pump chamber 436, and the regulator 432 is disposed within the pump chamber 436.

In response to a magnetic field generated by the control device 104, the regulator 432 moves to a position that creates a vacuum to draw fluid from the drug reservoir 414 into the pump chamber 436. In response to another change in the control device 104, the regulator 432 moves to a different position that results in an injection of the fluid past the valve 435 and out of the drainage tube 416. By controlling the amount of regulator displacement, the volume or dose of each injection can be carefully controlled. Also, by controlling the timing of the actuation with the control device 104, the injection frequency can also be controlled.

In some embodiments, the drug reservoir 414 includes a collapsible volume. The collapsible volume may include any known system for having a volume shrink as the drug is emitted from the system to the patient. In one embodiment, the collapsible volume is formed of an elastic bag containing the drug in the drug delivery device. Other collapsible volumes may be used. In some embodiments, the fluid is pressurized by the collapsible volume and the flow system 430 is used to control the dosage of the drug to the patient.

In an exemplary scenario, a healthcare provider can evaluate the current IOP and determine whether the aqueous humor is draining from the anterior chamber 70 in a desirable fashion. If not, the healthcare provider may determine that a drainage device may be implanted in the patient's eye. This may alleviate immediate pressure and careful control of the flow system with the control device may provide controlled drainage from the anterior chamber to the drainage site. Over time, the IOP may gradually rise due to resistance of outflow as a result of scarring at the drainage site (i.e., scarring or fibrosis of the bleb). The increase in drainage site pressure may hinder the passive flow of fluid through the drainage device 102 by decreasing the pressure differential across the drainage device 102. This results in a gradual increase in IOP.

The healthcare provider may monitor drainage to determine whether the aqueous humor is draining appropriately from the eye through the drainage device (e.g., if the IOP is not within a desired range, as determined by pressure measurements by the atmospheric pressure sensor 130 on the control device 104 and the anterior chamber pressure sensor on the drainage device). In some embodiments, the pressure measurements may be wirelessly communicated to the control device 104 from the drainage device using methods known in the art. In some embodiments, the control device emits RF transmissions, infrared signals, or other signals or fields and the drainage device harvests power from the transmissions to power the sensors on the device and to power active valves that may be on the device.

If IOP is higher than desired, the healthcare provider may pump fluid from the anterior chamber using the flow system described herein to effect a pressure change to the desired IOP. To do this, the user may alternatingly power the control device 104 to provide an energy field that alternatingly attracts and repels the metallic element creating a pumping effect. The systems disclosed herein may be used as a one-way reciprocating pump or may be used as a one-way control valve.

In some embodiments, the control device 104 may be programmed (e.g., via the processor 122) to activate the actuator 128 when the IOP surpasses a predetermined threshold value. Likewise, in some embodiments, the control device 104 may be programmed (e.g., via the processor 122) to deactivate the actuator 128 when the IOP falls below a predetermined threshold value. In some embodiments, these IOP threshold values or predetermined acceptable IOP ranges may be stored in the memory 124. In this fashion, the control device 104 enables the user to change how the drainage device 102 responds to the pressure differential across the flow system based on the changes in the IOP. The control device may be programmed by a health care provider to tailor treatment to a particular patient's needs and/or to selectively implement at any of a plurality of different control algorithms for IOP control.

Because the sensors are arranged to detect pressures that may be used to calculate IOP, some embodiments of the system operate as a closed-loop control where the measured data is used to set or control the control device 104, which is then modifies the fluid flow. Subsequent measurements may continue to be used to provide the closed-loop to stabilize or maintain IOP within a desired range.

In embodiments using electromagnets on the control system, the control system either attracts or repels the actuator in the drainage device. Doing this, the actuator increases or decreases the volume of the pump chamber of the device. As the volume increases, fluid is drawn through the one-way check valve into the chamber. As the volume decreases, the fluid in the pump chamber is forced through the one way check valve toward the drainage site. When used with a drug delivery device, the control system 104 may include stored treatment plans that include information such as dosage levels and a schedule to provide a suitable dose when desired. Some embodiments have regulator settings in place of dosage levels.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A system for treatment of an ocular condition of a patient, comprising:
   a flow device sized for implantation into the eye of the patient and including:
   a housing including an inlet port and an outlet port;
   a fluid flow passageway extending through the housing from the inlet port to the outlet port to allow the flow of fluid from the inlet port to the outlet port; and
   a flow system disposed within the flow device, the flow system including a regulator having a magnetic element, wherein the regulator comprises a flexible membrane being displaceable in the fluid flow passageway to affect flow through the fluid flow passageway, the magnetic element forming a rigid portion that is part of the flexible membrane; and
   a control device physically separate from the flow device and configured to be disposed outside the eye, the control device comprising a magnetic field generating actuator configured to act on the magnetic element to adjust the regulator in the flow system to selectively adjust flow through the flow device in response to changes in intraocular pressure.

2. The system of claim 1, wherein control device comprises an eyeglass frame.

3. The system of claim 1, wherein control device comprises a wearable article.

4. The system of claim 3, wherein the wearable article is one of a hat and a headband.

5. The system of claim 1, wherein the regulator includes a portion formed in the shape of an arch in cross-section, the magnetic element being disposed on the arch in a location that the arch displaces in a direction transverse to the flow direction in order to selectively restrict and allow fluid flow.

6. The system of claim 1, wherein the regulator is a flexible membrane portion and is configured to flex and move through the fluid flow passageway in the direction of the actuator when subjected to a magnetic field.

7. The system of claim 1, wherein the flow system comprises:
   a first one-way valve disposed upstream from the regulator in the fluid flow passageway; and
   a second one-way valve disposed downstream from the regulator in the fluid flow passageway, the regulator being actuatable to create a pumping effect with the first and second one-way valves.

8. The system of claim 1, wherein the control device comprises a power source larger than the flow device, the power source being configured to power the magnetic field generator.

9. The system of claim 7, wherein the flow device comprises:
   a first sensor configured to detect pressure representative of pressure in an anterior chamber of the eye, wherein the first sensor is disposed upstream from the first one-way valve; and
   a second sensor configured to detect pressure representative of pressure in a drainage site, wherein the second sensor is disposed downstream from the second one-way valve.

10. The system of claim 9, wherein the control device emits RF transmissions and wherein the flow device harvests power from the transmissions to power the first and second sensors.

11. A system for treatment of an ocular condition of a patient, comprising:
   a housing including an inlet port and an outlet port;
   a reservoir for maintaining a drug;
   a fluid flow passageway extending through the housing from the inlet port to the outlet port to allow the flow of fluid from the inlet port to the outlet port;
   a flow system disposed within the housing, the flow system including a regulator having a magnetic element, wherein the regulator comprises a flexible membrane that is displaceable in the fluid flow passageway to affect flow through the fluid flow passageway, the magnetic element forming a part of the flexible membrane; and a control device physically separate from the housing and configured to be disposed outside the patient, the control device comprising a magnetic field generating actuator configured to act on the magnetic element to adjust the regulator in the flow system to selectively adjust flow through the housing.

12. The system of claim 11, wherein control device comprises a wearable article.

13. The system of claim 12, wherein the wearable article is one of a hat and a headband.

14. The system of claim 11, wherein the flexible membrane includes a portion formed in the shape of an arch in cross-section, the magnetic element being disposed on the arch in a location that the arch displaces in a direction transverse to the flow direction in order to selectively restrict or allow fluid flow.

15. The system of claim 11, wherein the reservoir for maintaining the drug includes a collapsible volume.

16. The system of claim 11, wherein the flow system comprises:
a first one-way valve disposed upstream from the regulator in the fluid flow passageway; and
a second one-way valve disposed downstream from the regulator in the fluid flow passageway, the regulator being actuatable to create a pumping effect with the first and second one-way valves.

17. A method of regulating fluid flow from an anterior chamber of an eye, comprising:

directing fluid through an implantable flow device including a housing defining a fluid flow passageway and including a flow system comprising a flexible membrane having a magnetic element that forms part of the flexible membrane and is responsive to a control device, wherein the control device is physically separate from the flow device and is configured to be disposed outside the eye to adjust flow through the fluid flow passageway; and
modifying an amount of drainage through the implantable flow device by creating a magnetic field with the control device.

18. The method of claim 17, wherein modifying the amount of drainage through the implantable flow device comprises activating an actuator to adjust the regulator to affect flow through the fluid flow passageway.

19. The method of claim 18, wherein modifying the amount of drainage through the implantable flow device comprises activating the actuator in response to the intraocular pressure exceeding a predetermined threshold.

20. The method of claim 19, wherein modifying the amount of drainage through the implantable flow device comprises activating the actuator to change the position of a sealing portion in the fluid flow passageway relative to the housing.

* * * * *